US012778445B2

(12) United States Patent
Qi et al.

(10) Patent No.: US 12,778,445 B2
(45) Date of Patent: Nov. 3, 2026

(54) NON-CONTACT, NON-RADIATION DEVICE THAT ACCURATELY LOCATES MULTIPLE IMPLANTS IN A PATIENT'S BODY

(71) Applicant: The University of Hong Kong, Hong Kong (CN)

(72) Inventors: Weichen Qi, Hong Kong (CN); Teng Zhang, Hong Kong (CN); Pui Yin Cheung, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 135 days.

(21) Appl. No.: 18/684,150

(22) PCT Filed: Jul. 28, 2022

(86) PCT No.: PCT/CN2022/108627
§ 371 (c)(1),
(2) Date: Feb. 15, 2024

(87) PCT Pub. No.: WO2023/020241
PCT Pub. Date: Feb. 23, 2023

(65) Prior Publication Data

US 2024/0423496 A1 Dec. 26, 2024

Related U.S. Application Data

(60) Provisional application No. 63/233,526, filed on Aug. 16, 2021.

(51) Int. Cl.
*A61B 5/06* (2006.01)

(52) U.S. Cl.
CPC .................................... *A61B 5/062* (2013.01)

(58) Field of Classification Search
None
See application file for complete search history.

(56) References Cited

U.S. PATENT DOCUMENTS

| | | | |
|---|---|---|---|
| 5,729,129 | A | 3/1998 | Acker |
| 5,944,023 | A | 8/1999 | Johnson et al. |

(Continued)

FOREIGN PATENT DOCUMENTS

| | | | |
|---|---|---|---|
| CN | 102793526 | B | 11/2012 |
| CN | 112932750 | A | 6/2021 |

(Continued)

OTHER PUBLICATIONS

International Search Report in corresponding International Application No. PCT/CN2022/108627, mailed Sep. 27, 2022, 3 pages.

(Continued)

*Primary Examiner* — Guerrier Merant
(74) *Attorney, Agent, or Firm* — Leason Ellis LLP

(57) ABSTRACT

A system and devices provide for accurate localization of orthopedic implants based on magnetic tracking approach (MTA) technology and without radiation. The system includes at least one magnetic beacon that is joined to an orthopedic screw/implant fixed to a patient's spine. A detector in the form of a magnetic sensor array detects the magnetic field from the beacon and produces an electrical signal in response thereto. A computer using a multi-objective magnetic location algorithm tracks the spatial position and movement of the beacon based on the electrical signal, and hence tracks the patient's spine.

15 Claims, 6 Drawing Sheets

(56) References Cited

U.S. PATENT DOCUMENTS

| | | | | |
|---|---|---|---|---|
| 8,046,050 | B2 | 10/2011 | Govari | |
| 9,623,208 | B2 | 4/2017 | Wright | |
| 10,254,833 | B2 | 4/2019 | Osman | |
| 2005/0080427 | A1 | 4/2005 | Govari et al. | |
| 2007/0225595 | A1 | 9/2007 | Malackowsky et al. | |
| 2007/0276218 | A1 | 11/2007 | Yellen | |
| 2008/0114270 | A1 | 5/2008 | Disilvestro et al. | |
| 2010/0249576 | A1 | 9/2010 | Askarinya et al. | |
| 2017/0079548 | A1* | 3/2017 | Silverstein | A61B 8/0841 |
| 2019/0223975 | A1* | 7/2019 | Agostinelli | A61B 5/062 |

FOREIGN PATENT DOCUMENTS

| | | | |
|---|---|---|---|
| DE | 102011013398 | A1 | 9/2011 |
| EP | 1803413 | B1 | 7/2007 |
| EP | 1570781 | B1 | 9/2009 |
| KR | 100972253 | B1 | 7/2010 |
| WO | 9608999 | A1 | 3/1996 |

OTHER PUBLICATIONS

Park et al. MagTouch: Robust Finger Identification for a Smartwatch Using a Magnet Ring and a Built-in Magnetometer. Proceedings of the 2020 CHI Conference on Human Factors in Computing Systems. 2020: 1-13.

Pham et al. A real-time localization system for an endoscopic capsule using magnetic sensors. Sensors, 2014, 14 (11): 20910-20929.

Su et al. Investigation of the relationship between tracking accuracy and tracking distance of a novel magnetic tracking system. IEEE Sensors Journal, 2017, 17(15): 4928-4937.

Sun et al. Passive magnetic-based localization for precise untethered medical instrument tracking. Computer methods and programs in biomedicine, 2018, 156: 151-161.

Tarantino et al. The myokinetic control interface: tracking implanted magnets as a means for prosthetic control. Scientific reports, 2017, 7(1): 1-11.

Taylor et al. Low-latency tracking of multiple permanent magnets. IEEE Sensors Journal, 2019, 19(23): 11458-11468.

Yang et al. A new tracking system for three magnetic objectives. IEEE Transactions on Magnetics, 2010, vol. 46, No. 12, pp. 4023-4029.

* cited by examiner

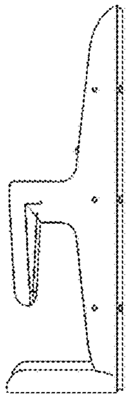
FIG. 3A
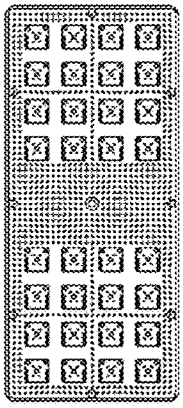
FIG. 3B
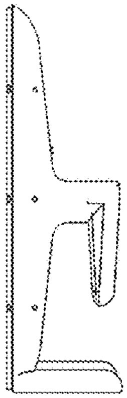
FIG. 3C
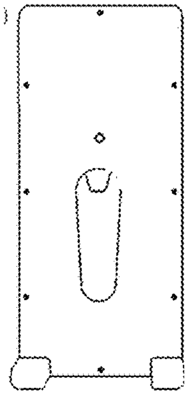
FIG. 3D
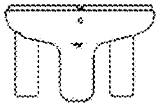
FIG. 3E
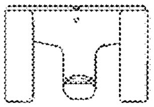
FIG. 3F
FIG. 3G
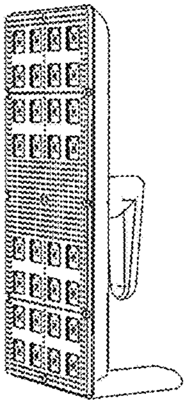

NON-CONTACT, NON-RADIATION DEVICE THAT ACCURATELY LOCATES MULTIPLE IMPLANTS IN A PATIENT'S BODY

CROSS-REFERENCE TO RELATED PATENT APPLICATIONS

This application is a U.S. National Phase Application under 35 U.S.C. § 371 of International Patent Application No. PCT/CN2022/108627 filed on Jul. 28, 2022 and claims the benefit of U.S. Provisional Patent Application No. 63/233,526 filed on Aug. 16, 2021, the entire contents of which are incorporated by reference for all purpose. The International Application was published in English on Feb. 23, 2023 as International Publication No. WO/2023/020241 under PCT Article 21(2).

FIELD OF THE INVENTION

The present invention relates to the accurate detection of the location of body implants and, more particularly, to a non-contact, non-radiation device for locating multiple implants in a patient's body.

BACKGROUND OF THE INVENTION

In some orthopedic treatments, multiple measurements of the affected site are needed to evaluate the patient's condition. The most common measurement means are X-ray, CT and other radiological imaging methods. However, the harmful effects of prolonged exposure of patients and operators to radiation needs to be considered in the application of radiography. For applications where repeated measurements are required over a limited period of time, non-radiation measurement techniques are safer than radiological ones. In addition, non-radiation measurement does not require expensive radiation sources, and the cost is lower, and it can be easily portable for use by surgeons.

The correction of scoliosis is a typical procedure that relies on non-radiometric measurements. Scoliosis is a common disease that harms adolescents and seniors. Severe scoliosis can affect the growth and development of young children and can cause musculoskeletal deformation. Severe cases can affect cardiopulmonary function. The key to the treatment of scoliosis is early detection and treatment. If lateral curvature of the spine occurs as a type of easy progression or if obvious progression occurs during observation, surgical treatment should be performed as soon as possible. Most surgical treatments rely on pedicle screws or anchors/buckles to fix metal bars/plates/wires or flexible ropes to the patient's spine. Then mechanical structures such as sliding rings, pawls and threads are extended to provide the force that needs to be applied to the spine to correct scoliosis.

Specific spinal parameters, such as the degree of correction of Cobb Angle, the high value added of T1~S1 vertebrae, etc., should be frequently measured to observe and quantitatively analyze the therapeutic effect during postoperative correction of scoliosis. In order to reduce the amount of radiation absorbed by the patient while taking the X-ray photography, special measurement tools are needed clinically. The most common measurement tool is a scoliosis meter. However, the measurement error of the device is large due to the subjective judgements required of the therapist and the influence of the patient's position. In the laboratory, some new measurement technologies based on video recognition or ultrasonic measurement have also been tried to evaluate the effect of surgical correction of scoliosis.

However, the accuracy and precision of these indirect measurement technologies are easily affected by external conditions: with an increase in the number of measurements and an extension of the interval between measurements, there are often errors and deviations in the results of multiple measurements.

Therefore, a measurement system that can quickly and accurately measure the correction volume of the spine after each correction is needed. Especially when using techniques that require multiple corrections (such as automatic extension rod technology and magnetic extension rods technology), real-time feedback of spinal parameters can improve the therapeutic effect. In the event of the recurrence and aggravation of deformity, or sticking, or other failure of distraction, the operator needs to quickly correct the scheme or stop the operation to ensure the safety of the correction

SUMMARY OF THE INVENTION

The present invention is a device and system based on magnetic tracking approach (MTA) technology for accurate localization of orthopedic implants without radiation. The invention uses MTA technology instead of radiological technology to measure patient spine parameters so as to avoid the effect of patient exposure to radiation. Specifically, a few magnetic beacons are placed inside a screw/implant, and the spatial position of the screw/implant is tracked with a handheld magnetic sensor array using a multi-objective magnetic location algorithm. The parameters of the patient's spine are generated by the multi-objective algorithm. As a result, the measurement accuracy is much higher than that of the prior art scoliosis meter, and it is not affected by the subjective considerations of the operator.

The sources of error in the measurement accuracy when using the present invention are mainly geomagnetic interference, sensor drift, manufacturing defects, etc. The existing MTA technology provides a good way to eliminate the system error as much as possible, so the use environment will not have a significant impact on the measurement.

The device and system form a non-contacting medical device with a localization sensitivity smaller than 0.1 mm at 1 degree. This novel system and the device have a significant clinical impact by providing an economical, portable and harmless method for monitoring the true performance (including extension accuracy and fixation stability) of the orthopedic implants.

The radiation-free, non-contact measuring device of the present invention can accurately locate multiple screws or implants in a patient's body, giving surgeons the ability to modify treatment plans in real time during procedures, such as scoliosis correction, in order to enhance treatment effectiveness and improve safety.

In addition to scoliosis, the system can also be used to treat other orthopedic diseases. In particular, the device can measure the position of implants other than pedicle screws and can track the movement of multiple implants. This technology has a wide range of applications in complex fracture correction, intelligent prosthetic limbs, wearable devices and other scenarios. The present invention is suitable for many surgical applications, including but not limited to (1) measuring the displacement parameters of the vertebrae during scoliosis correction, (2) measuring the elongation of the bone during limb extension, and (3) the navigation of surgical instruments.

The various novel features of the present invention can be summarized in following keywords:

Harmless. MTA technology replaces radiography to locate screws and implants with magnetic beacons inside the patient.

Portable. Handheld devices based on embedded systems communicate with computers through Bluetooth technology.

Economical. The device and system are manufactured using commercial components at low cost.

User-friendly. The device works without the intervention of the operator, and automatically calculates and outputs the measured parameters.

BRIEF SUMMARY OF THE DRAWINGS

The foregoing and other objects and advantages of the present invention will become more apparent when considered in connection with the following detailed description and appended drawings in which like designations denote like elements in the various views, and wherein:

FIG. 3A-3F are hexahedral orthographic views of the handheld detector and FIG. 3G is an oblique view of the detector;

DETAILED DESCRIPTION

Figure 1A:
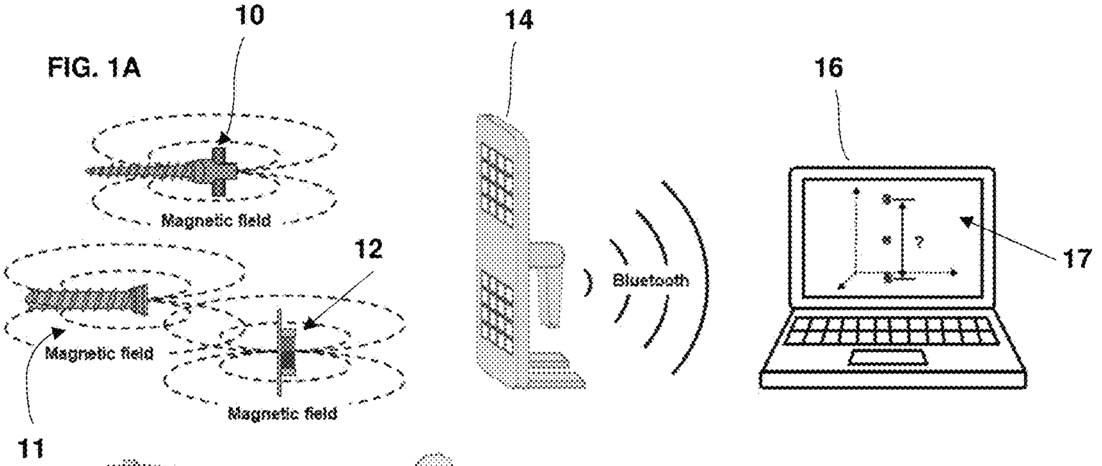
FIG. 1A shows the overall in vivo implant tracking system of the present invention.

The in vivo general positioning system (in vivo GPS) of the present invention is composed of three parts, i.e. magnetic beacons, a detector and a computer. FIG. 1A shows the overall in vivo implant tracking system of the in vivo GPS. Magnetic beacons 10, 11, 12 are placed on the pedicle screws or other orthopedic implants which are then located in the patient's body, e.g., on the patient's spine. The detector 14 detects the magnetic field surrounding the beacons and transports the data to the computer 16 by Bluetooth. Then the computer 16 uses an MTA algorithm to locate the spatial positions of the magnetic beacons and outputs the parameters of, e.g., scoliosis correction or the implant movement. The output may be on the display screen 17 of computer 16.

Figure 1B:
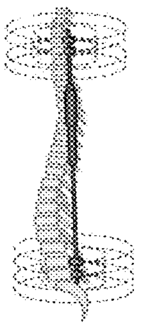
FIG. 1B illustrates the displacement parameters of the vertebrae during scoliosis correction.
Figure 1C:
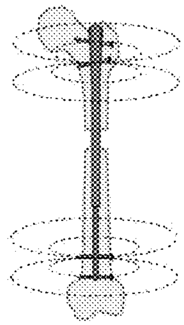
FIG. 1C illustrates the elongation of the bone during limb extension.
Figure 1D:
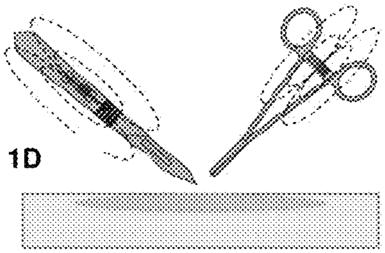
FIG. 1D shows the navigation of surgical instruments.

Some exemplary application scenarios of this system are presented in FIGS. 1B, 1C and 1D, which show, respectively, (1) measuring the displacement parameters of the vertebrae during scoliosis correction, (2) measuring the elongation of the bone during limb extension, and (3) the navigation of surgical instruments.

Figure 2A:
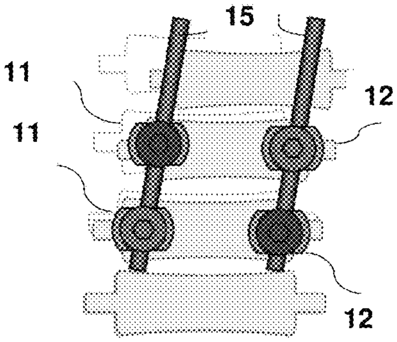
FIG. 2A is the front view of magnetic beacons on pedicle screws.
Figure 2B:
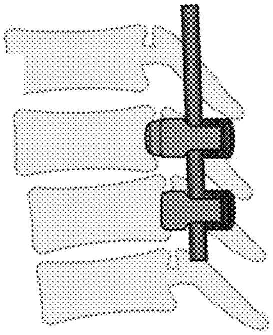
FIG. 2B is the lateral view of the magnetic beacons on pedicle screws and FIG. 2C shows the detailed structure of the magnetic beacon.
Figure 2C:
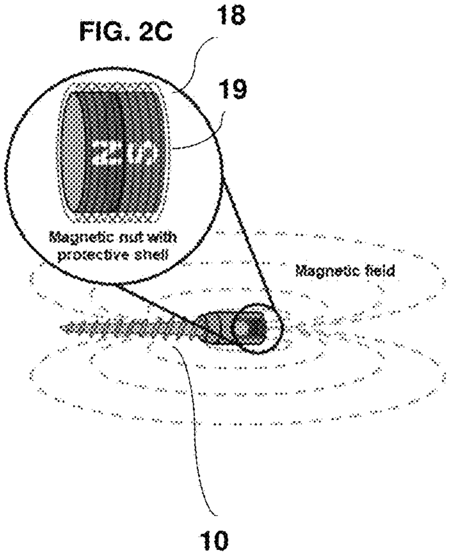

FIG. 2A is a front view of magnetic beacons 11, 12 on pedicle screws connected to rods 15 and FIG. 2B is a lateral view of the magnetic beacons on the pedicle screws connected to the rods. FIG. 2C shows the detailed structure of a magnetic beacon 10. The magnetic beacon is a magnetic nut 19 wrapped in a protective shell 18. The magnetic nut is made of a strong permanent magnet containing neodymium. The protective shell is made of bioinert materials approved by the FDA, including but not limited to titanium or its alloy and Polytetrafluoroethylene (PTFE) polymer. For the convenience of distinguishing them, magnetic beacons are divided into N type and S type according to the direction of the magnetic field, which is represented by red (N type) and blue (S type) in the FIG. 2.

Figure 4A:
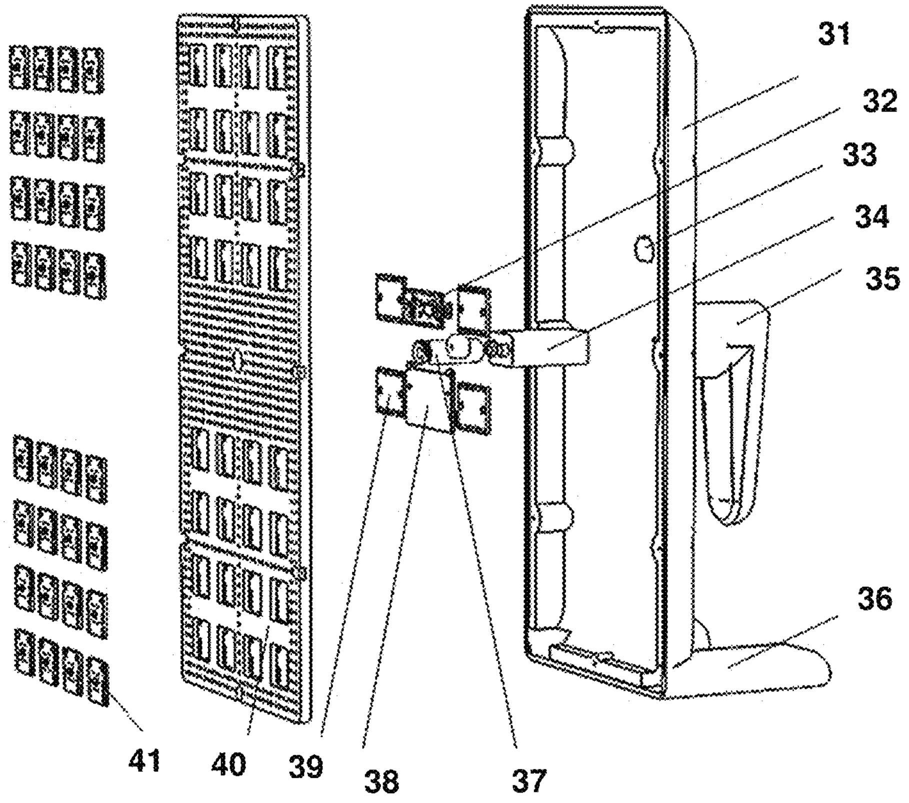
FIG. 4A is an exploded view of the internal structure of the detector and FIG. 4B shows the detector emitting a cross-shaped laser beam onto the back of a patient.
Figure 4B:
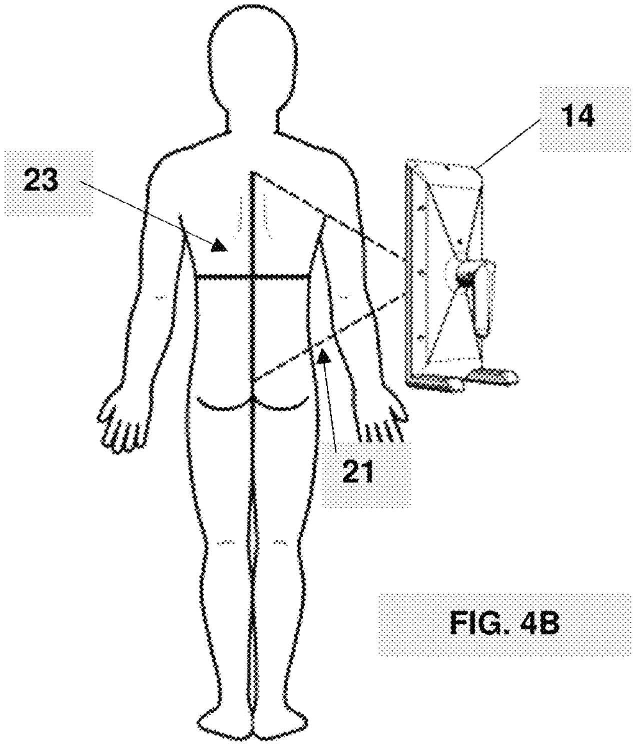

FIG. 3 shows hexahedral orthographic views (FIGS. 3A-3F) and FIG. 2G is an oblique view of the detector 14. FIG. 4A shows the internal structure of the detector 14. All electronic components (32, 33, 34, 37, 38, 39, 41) are placed on a polymethyl methacrylate (PMMA) mainboard 40 and are protected by a plastic outer shell 31 to avoid damage from water, dust, static electricity, and unexpected impact. The handle 35 and supporting legs on the outer shell 31 allow the detector 14 to be placed upright on a desktop or to be easily held by the user. Further, the detector 14 can also be placed horizontally on the tabletop for calibration. A laser aimer 37 emits a cross-shaped laser beam 21 as the detector is used, allowing the user to locate the position of the spine on the back skin of the patient and show a detectable range 23. Under the control of a microcontroller unit (MCU), a buzzer 38 sends out different audio prompts to aid the user in knowing the working state of the detector.

Figure 5:
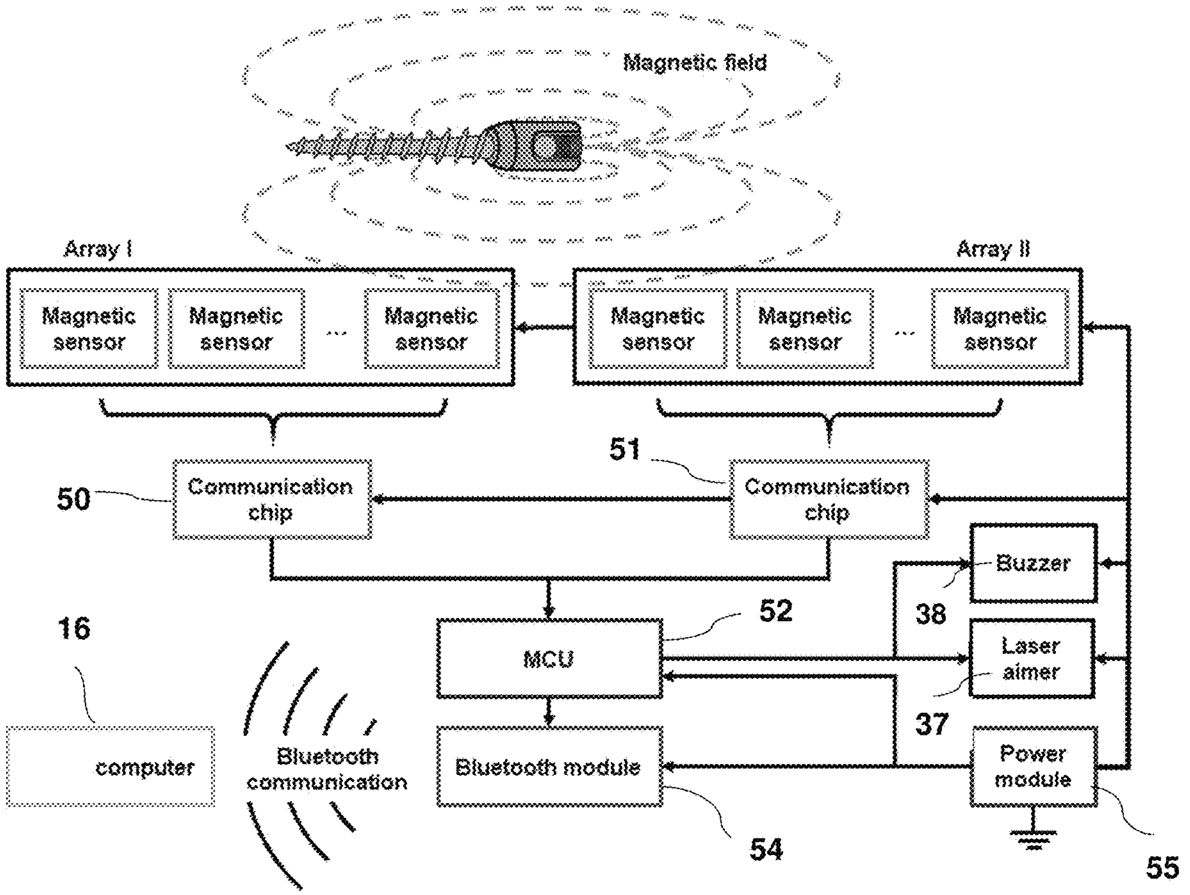
FIG. 5 is a block diagram of the electronic components in the detector.

FIG. 5 is a block diagram of the electronic components in the detector. Each communications chip 50, 51 controls a 4 by 4 sensor array (Array I, Array II), allowing each sensor to output readings in sequence. Then the two communication chips alternately transmit data to the MCU 52. The MCU collects all the data and transmits the data to the computer 16 through the Bluetooth module 54. Meanwhile, the MCU 52 controls the operation of laser aimer 37 and buzzer 38. The power module 55 supplies power to all of the electronic components and manages power under the control of the MCU.

Figure 6A:
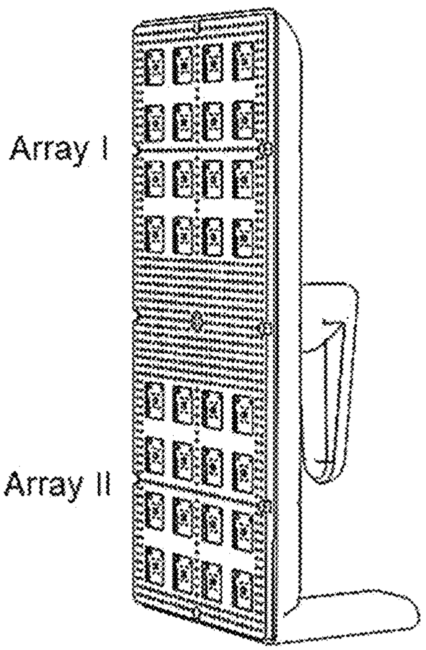
FIG. 6A an illustration of the detector with two sensor arrays and FIG. 6B shows Array I covering beacons A and A', and magnet C on one magnetic growth rod, Array II covering beacons B and B', and magnet C' on the other magnetic growth rod.
Figure 6B:
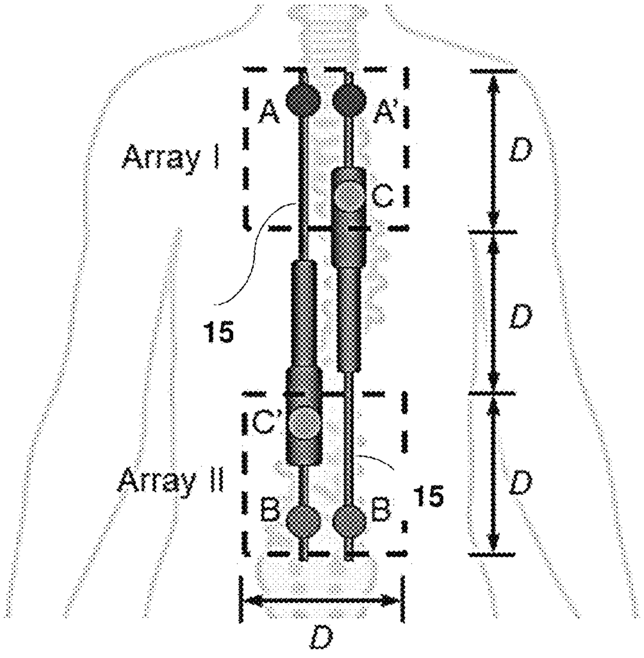

In one embodiment of the present invention two detector arrays, i.e., Array I and Array II, are used (FIG. 6A), instead of a single large array, to improve positioning accuracy and enhance the ability to distinguish between approaching targets. During scoliosis correction, pedicle screws (A, A', B, B', C. C') attached to extension rods 15 are centered at the upper and lower ends of the spine (FIG. 6B). Therefore, the use of two arrays allows for the concentration of as many magnetic sensors as possible close to the target in order to receive the magnetic field from the magnetic beacons and to ensure measurement accuracy and resolution, thus improving the positioning accuracy. Meanwhile, the concentration of sensors is beneficial to enhance the ability of the device to distinguish multiple close targets, particularly two close screws on the same vertebra. The distance between the two square arrays (Array I and II) is equal to their side lengths D and they share coordinates.

Figure 7A:
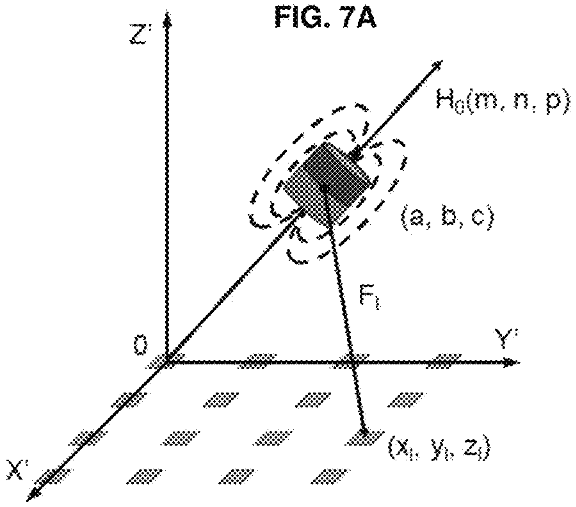
FIG. 7A is a schematic diagram of MTA technology and FIG. 7B shows the output of measurement parameters of the spine during the correction of scoliosis based on an MTA algorithm program run on a computer.
Figure 7B:
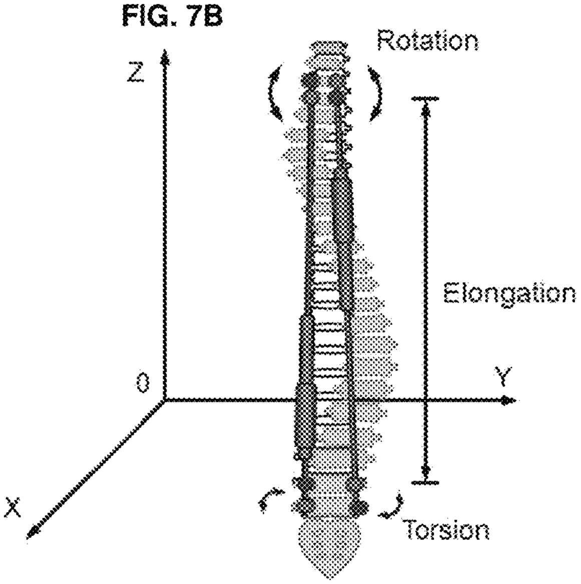

As depicted in FIG. 7A, the coordinates of the center position of a magnetic beacon are (a, b, c), the position of the lth magnetic sensor is (xl, yl, zl) and the orientation of the beacon is H0=(m, n, p)T. Fl denotes the vector from (a, b, c) to (xl, yl, zl). In the tracking process, the position of the beacon is changing all the time, which is the variable to be estimated in the magnetic tracking approach (MTA) system. The position of beacons is denoted as v=[a, b, c, m, n, p]T. The function of the MTA algorithm is to solve for the position v of the beacon according to the readings from all of the magnetic sensors in the array. After the positions of all the beacons in the coordinate system have been figured out, the measurement parameters of the spine during the correction of scoliosis are also output, including rotation, elongation, torsion, etc. (FIG. 7B).

Figures 8A, 8B, 8C, 8D:
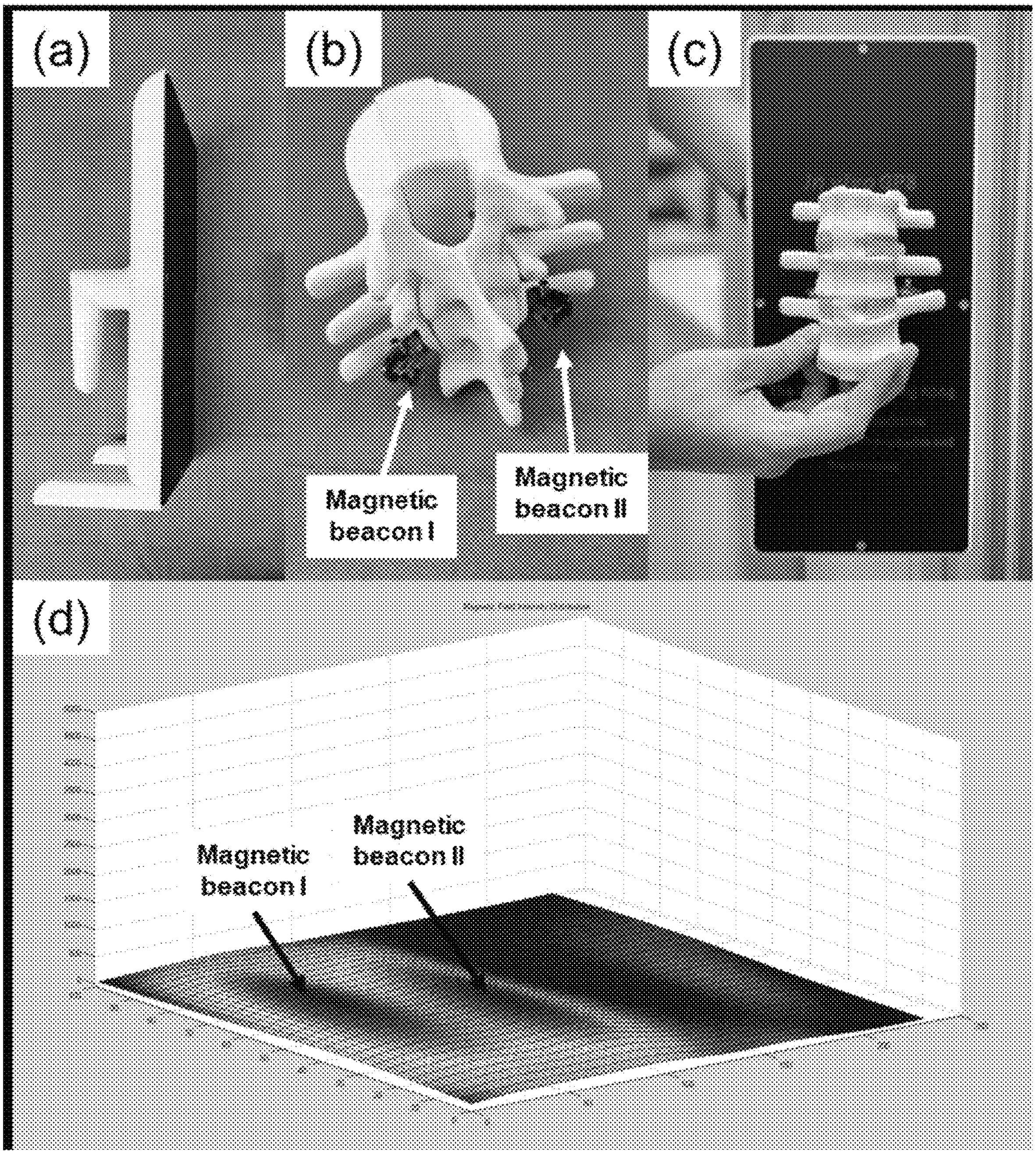
FIG. 8A is a prototype of the detector of the present invention.
FIG. 8B shows a downward perspective view of two magnetic screws driven into a part of a vertebral dummy.
FIG. 8C shows a side view of the vertebral dummy.
FIG. 8D illustrated the output of the computer program of the present invention showing the locations of the beacons.

A prototype of an embodiment of this invention was manufactured to verify its basic functions and effectiveness. FIG. 8A shows a prototype of the detector of the in vivo general positioning system (GPS). This prototype can be used normally and has all the basic functions of the invention. In testing the prototype, magnets were placed on the ends of pedicle screws to simulate magnetic beacons (beacon I and beacon II), and two of these magnetic screws were driven into a part of a vertebral dummy (FIG. 8B). Then this dummy with magnetic screws was placed in front of the detector of the prototype to verify the ability of the prototype to distinguish between two nearby targets (FIG. 8C). The results shown in FIG. 8D illustrate that the computer and its multi-objective algorithm program have a good ability to distinguish between two adjacent targets.

The prototype test was in part designed to predict the effect of soft tissue on location accuracy. This was achieved with animal experiments. In building the prototype materials were selected and calibration procedures were used to eliminate the effects of the geomagnetic field and the surrounding magnetic field on the device.

The device is required to distinguish between two adjacent pedicle screws (distance is 30-50 mm) on the same vertebra. The precision and resolution parameters of the prototype device design are as follows: within the detection range of 600*50 mm, the range resolution is no more than 0.1 mm, and the angular resolution is no more than 1 degree.

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A system for accurate localization of orthopedic implants based on magnetic tracking approach (MTA) technology and without radiation, comprising:

at least one magnetic beacon that is joined to an orthopedic screw/implant that is fixed to a patient's spine;

a detector in the form of a magnetic sensor array for detecting a magnetic field from the beacon and producing an electrical signal in response thereto, said magnetic sensor array being in the form of two separated sensor arrays; and a processor using a multi-objective magnetic location algorithm to track the spatial position and movement of the beacon based on the electrical signal, and hence the patient's spine.

2. The system for accurate localization of orthopedic implants of claim 1 wherein there are a plurality of beacons at various places on the patient's spine.

3. The system for accurate localization of orthopedic implants of claim 2 wherein the spatial position and movement are capable of indicating all of (1) the displacement parameters of the vertebrae during scoliosis correction, (2) the elongation of the bone during limb extension, and (3) the navigation of surgical instruments.

4. The system for accurate localization of orthopedic implants of claim 2 wherein the measurement parameters of the spine include displacement, rotation, elongation and torsion.

5. The system for accurate localization of orthopedic implants of claim 1 wherein the detector is handheld and can be moved over the patient's body, and wherein the detector sends the electrical signal to the processor by Bluetooth technology.

6. The system for accurate localization of orthopedic implants of claim 1 wherein the magnetic beacon is a magnetic nut wrapped in a protective shell and the magnetic nut is made of a permanent magnet.

7. The system for accurate localization of orthopedic implants of claim 6 wherein the magnet contains neodymium.

8. The system for accurate localization of orthopedic implants of claim 6 wherein the magnetic nut is either N-type or S-type.

9. The system for accurate localization of orthopedic implants of claim 6 wherein the protective shell is made Polytetrafluoroethylene (PTFE) polymer.

10. The system for accurate localization of orthopedic implants of claim 1 wherein the detector further includes a laser aimer that emits a cross-shaped laser beam as the detector is used, allowing the user to locate the position of-the spine on the back skin of the patient and show a detectable range.

11. The system for accurate localization of orthopedic implants of claim 1 further including a buzzer that sends out different audio prompts to aid the user in knowing the status of the detector.

12. The system for accurate localization of orthopedic implants of claim 1 wherein the two separated sensor arrays are in the form of two square sensor arrays on the detector that are separated from each other by their side lengths, said arrays sharing lateral coordinates on the detector.

13. The system for accurate localization of orthopedic implants of claim 12, wherein the system is capable of distinguishing between two adjacent implants in a distance between 30 and 50 mm in a range of 600*50 mm with a range resolution of no more than 0.1 mm and an angular resolution of no more than 1 degree.

14. The system for accurate localization of orthopedic implants of claim 1 wherein the two separated sensor arrays are in the form of two sensor arrays on the detector and wherein the detector has circuits for sending the sensor signals to the processor comprising:

two communications chips which are separately connected to the two sensor arrays, said communications chips allowing each sensor to output readings in an alternating sequence;

a microcontroller unit that alternately collects the outputs of the communications chips and transmits the data to the computer through a Bluetooth module.

15. The system for accurate localization of orthopedic implants of claim 14 further including a laser aimer that emits a cross-shaped laser beam as the detector is used, allowing the user to locate the position of the spine on the back skin of the patient and show a detectable range, and a buzzer that sends out different audio prompts to aid the user in knowing the status of the detector, wherein the laser aimer and buzzer are under the control of the microcontroller.

* * * * *